United States Patent [19]
Doner et al.

[11] Patent Number: 4,781,850
[45] Date of Patent: Nov. 1, 1988

[54] GREASE COMPOSITIONS CONTAINING BORATED CATECHOL COMPOUNDS AND HYDROXY-CONTAINING SOAP THICKENERS

[75] Inventors: John P. Doner, Sewell; Andrew G. Horodysky, Cherry Hill; John A. Keller, Jr., Pitman, all of N.J.

[73] Assignee: Mobil Oil Corporation, New York, N.Y.

[21] Appl. No.: 24,235

[22] Filed: Mar. 10, 1987

Related U.S. Application Data

[63] Continuation-in-part of Ser. No. 769,837, Aug. 27, 1985, Pat. No. 4,655,948.

[51] Int. Cl.$^4$ .......................................... C10M 125/26
[52] U.S. Cl. ...................... 252/49.6; 252/32; 252/54
[58] Field of Search .................. 252/49.6; 524/552; 526/298

[56] References Cited

U.S. PATENT DOCUMENTS

| | | | |
|---|---|---|---|
| 2,053,474 | 9/1936 | Graves et al. | 260/98 |
| 2,813,830 | 11/1957 | Trautman | 252/49.6 |
| 2,815,325 | 12/1957 | Pohorilla et al. | 252/42.1 |
| 2,943,054 | 6/1960 | Worth | 252/40.7 |
| 3,125,525 | 3/1964 | Siegart et al. | 252/33.6 |
| 3,224,971 | 12/1965 | Knowles et al. | 252/46.3 |
| 3,361,672 | 1/1968 | Andress et al. | 252/49.6 |
| 3,446,808 | 5/1969 | Cyba | 260/250 |
| 3,697,574 | 10/1972 | Piasek | 260/462 R |
| 3,704,308 | 11/1972 | Piasek et al. | 260/462 R |
| 3,923,712 | 12/1975 | Vickery | 524/552 |
| 4,016,092 | 4/1977 | Andress | 252/32.5 |
| 4,071,548 | 1/1978 | Okamoto | 260/462 R |
| 4,182,823 | 1/1980 | Schoenberg | 526/298 |
| 4,426,305 | 1/1984 | Malec | 252/49.6 |
| 4,655,948 | 4/1987 | Doner et al. | 252/49.6 |

FOREIGN PATENT DOCUMENTS

| | | |
|---|---|---|
| 0067002 | 12/1982 | European Pat. Off. |
| 0075478 | 3/1983 | European Pat. Off. |
| 0134063 | 3/1985 | European Pat. Off. |
| 2103651 | 2/1983 | United Kingdom |
| 2107734 | 5/1983 | United Kingdom |
| 2125431 | 3/1984 | United Kingdom |

*Primary Examiner*—William R. Dixon, Jr.
*Assistant Examiner*—Ellen McAvoy
*Attorney, Agent, or Firm*—Alexander J. McKillop; Michael G. Gilman; Van D. Harrison, Jr.

[57] ABSTRACT

Disclosed is a grease composition comprising a major proportion of a grease, a hydroxy-containing soap thickener and a minor amount of a boronated catechol compound. The hydroxy-containing soap thickener and boronated catechol (ortho dihydroxybenzene) compound are each added in amounts sufficient to increase the dropping point of the grease an appreciable amount. The catechol (ortho dihydroxybenzene) compounds useful in this invention include catechol borates, catechol-alcohol borate compounds and catechol-amine borate compounds.

13 Claims, No Drawings

GREASE COMPOSITIONS CONTAINING BORATED CATECHOL COMPOUNDS AND HYDROXY-CONTAINING SOAP THICKENERS

CROSS REFERENCE TO RELATED APPLICATIONS

This is a continuation-in-part of our copending application Ser. No. 769,837, filed Aug. 27, 1985, now U.S. Pat. No. 4,655,948.

BACKGROUND OF THE INVENTION

1. Nature of the Invention

The invention is concerned with grease compositions. More particularly it is concerned with a grease composition comprising oil, hydroxy-containing soap thickener and certain borated organic compounds and, optionally, phosphorus and sulfur moieties.

2. Prior Art

The publication "Manufacture and Application of Lubricating Grease by C. J. Boner (Reinhold Publishing Company) 1954, pp. 155 and 436, 437 disclose the use of lithium soaps in grease making. The publication "Lubricant Additive" by C. V. Smalheer et al (Leyuis-Hiles Co.) 1967, pp. 1–11, discloses the use of phosphonates and thiophosphonates as additives in lubricants. "Condensed Chemical Dictionary" 9th Edition, (Van Nostrand Reinhold Company) at pages 520 and 938 discloses the use of lithium hydroxystearate in grease making and zinc dialkyldithiophosphate as a lube oil additive.

These references, the publications by Boner and by Smalheer et al, and the "Condensed Chemical Dictionary" reference are incorporated herein by reference.

SUMMARY OF THE INVENTION

In accordance with this invention, there is provided an improved grease composition comprising a major proportion of a grease, a hydroxy-containing soap thickener and a minor amount of boronated catechol compound. The hydroxy-containing soap thickener and boronated catechol (ortho dihydroxybenzene) compound are each added in amounts sufficient to increase the dropping point of the grease an appreciable amount. Generally the increase will be at least 15° F. but it can be as great as 200° F. to 250° F. or more.

Description of the Invention

The catechol (ortho dihydroxybenzene) compounds useful in this invention include:
 (a) catechol borates
 (b) catechol-alcohol borate compounds; and
 (c) catechol-amine borate compounds.

The Catechol Borate, Catechol-Amine-Borate, and Catechol-Alcohol-Amine Borate Compounds The catechol borate and the borated catechol alcohol or borated catechol amine compounds are obtained by the following reactions yielding these products shown:

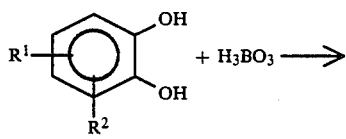

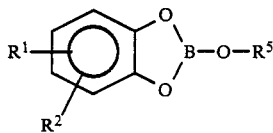

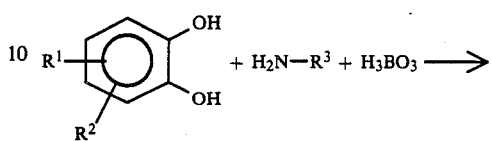

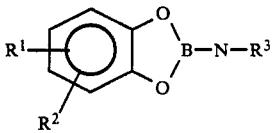

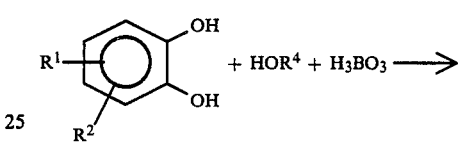

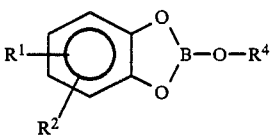

where $R^1$ and $R^2$ can each be hydrogen or $C_1$–$C_{40}$ hydrocarbyl. $R^1$ and $R^2$ optionally can also contain sulfur, oxygen, nitrogen or other such groups as long as the presence of these elements does not negatively affect performance of the additive compound.

$R^3$ can be $C_1$–$C_{40}$ hydrocarbyl and can contain, additionally, oxygen, sulfur and/or nitrogen-containing moieties.

$R^4$ can be $C_1$–$C_{40}$ hydrocarbyl and can contain, additionally, oxygen, sulfur and/or nitrogen-containing moieties.

$R^5$ can be boron and/or catechol and/or ester and/or hydroxyl-containing moieties.

Thus the family of catechol borates useful in this invention can be represented by the following nonlimiting generic structure:

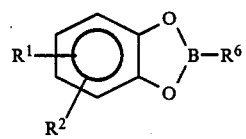

where $R^6$ can be $R^3$, $R^4$, or $R^5$, and can additionally contain oxygen, nitrogen, sulfur and boron as described above.

$R^6$ can also be a hydrogen or hydroxyl substituent on B (boron) atom.

The reaction to make these borated compounds, as well as mixtures of catechol borates, can be carried out by mixing the two or three reactants in equal mole proportions or with an excess of up to 1000 mole percent of one or two of the reactants. The reaction is carried out at a temperature of 70° to 270° C.

Useful amines include hydrocarbyl amines, such as oleyl amine, stearyl amine, tallow amine, hydrogenated tallow amine, aniline, and other aromatic amines; diamines, such as N-coco-1,3-propylenediamine, and N-coco-1,2-ethylenediamine, and the N-linoleyl-, N-oleyl-, N-stearyl-, N-isostearyl-, N-tallow-, N-triisostearyl-, N-decyl-, counterparts thereof, N-hydrocarbyloxylpropyl hydrocarbylenediamines, triamines. polyamines, and derivatives of polyamines, including polyethyleneamine derivatives of diethylenetriamine, triethylene, tetramine, and tetraethylenepentamine. Also included are hydroxyl-containing and sulfur-containing amines.

Useful alcohols include alkanols, unsaturated alcohols, cyclic alcohols, sulfur-containing alcohols, alkoxylated and polyalkoxylated alcohols, phenols, sulfur-containing phenolics, and mixtures of the above. Examples include oleyl alcohol, stearyl alcohol, isostearyl alcohol, mixed $C_{15}$–$C_{18}$ alcohols, phenol, dodecylphenol, nonylphenol, mixed $C_9$–$C_{11}$ alkanol diethoxylates and the like, as well as alcohols containing nitrogen or sulfur atoms in their structure.

Useful hydroxy esters include ethyleneglycol monooleate, diethyleneglycol monooleate, glycerol dioleate, glycerol monooleate, trimethylolpropane dioleate, pentaerythritoltrioleate, and corresponding stearates, isostearates, tallowates, and other $C_{10}$–$C_{20}$ acid derived esters.

The borating agent can be an appropriate boron compound, including, but not limited to, boric acid, boric oxide, metaborates or a compound of the formula $$(R^7O)_xB(OH)_y$$

wherein $R^7$ is a $C_1$ to $C_6$ alkyl group, x is 0 to 3 and y is 0 to 3, their sum being 3. As indicated by the formula, included are boric acid and the alkyl borates, such as the mono-, di- and trialkyl borates.

A narrow class of thickening agents is used to make the grease of this invention. The thickening agents contain at least a portion of alkali metal, alkaline earth metal or amine soaps of hydroxyl-containing fatty acids, fatty glycerides and fatty esters (including methyl and ethyl esters) having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid. Mixtures of soap thickeners can also be used. Poly-hydroxy fats and acids can also be used.

The entire amount of thickener need not be derived from the aforementioned members. Significant benefit can be attained using as little there of as about 3 to 15 percent by weight of the total thickener and up to 100% of the total thickener, the thickener itself making up 2 to 30 percent of the grease composition. A complementary amount, i.e., up to about 85% by weight of a wide variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

Greases benefiting from the borated additive can be produced by any of the commonly used manufacturing techniques which include open or closed kettle saponification. Saponifications can also be carried out in pressure vessels, commonly known as contactors, at a variety of temperature and pressures. Continuous grease production type equipment can also be used to produce the grease which will be treated with the borated additive. Operating temperatures and pressures are variable as with the conditions normally used to carry out the saponification for the type of reactants involved. The temperatures will generally range from room temperature 25° C. to 232° C. Pressures will range from 190 psig to as low as vacuum.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline, as well as certain hydrophobic clays. These thickening agents can be prepared from clays which are initially hydrophilic in character, but which have been converted into a hydrophobic condition by the introduction of long-chain hydrocarbon radicals into the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. These methods of grease manufacture, being well known to those skilled in the art, are believed to require no further discussion, and does not form a part of the present invention.

The third member(s) that may be present in the grease composition are the phosphorus and sulfur moieties. Both of these can be present in the same molecule, such as in a metal or non-metal phosphorodithioate of the formula $$\left[(R^8O)_2\overset{Z}{\underset{\|}{P}}Z\text{--}\right]_n\text{--M}$$

wherein $R^8$ is a hydrocarbyl group containing 3 to 18 carbon atoms. This hydrocarbyl group can also contain sulfur, and/or a hydroxyl or ester group. M is preferably a metal, but may be a non-metal, such as one of those mentioned hereinbelow, n is the valence of M and Z is oxygen or sulfur, at least Z being sulfur. The phosphorodithioate may also be complexed as in a zinc acetate complexed zinc phosphorodithioate.

In this compound, $R^8$ is preferably an alkyl group and may be a propyl, butyl, pentyl, hexyl, octyl, decyl, dodecyl, tetradecyl or octadecyl group, including those derived from isopropanol, propanol, butanol, isobutanol, sec-butanol, 4-methyl-2-pentanol, 2-ethylhexanol, oleyl alcohol, and mixtures thereof. Further included are alkaryl groups such as butylphenyl, octylphenyl, nonylphenyl and dodecylphenyl groups.

The phosphorodithioate may also be derived from a diol such as 1,2-decanediol or 1,3-pentanediol or can be derived from hydroxyesters and can additionally contain other elements such as sulfur.

The metals embraced by M include those in Groups IA, IIA, IIB, and VIII of the Periodic Table. Some that may be mentioned are lithium, sodium, calcium, zinc, cadmium, silver, gold and molybdenum. Non-metallic ions include organic groups derived from vinyl esters such as vinyl acetate, vinyl ethers such as butyl vinyl ether and epoxides such as propylene oxide and 1,2-epoxydodecane. The non-metallic ions may also be derived from nitrogenous compounds such as those derived from hydrocarbyl amines and diamines, including oleylamine and N-oleyl-1,3-propylenediamine and such as the imidazolines and oxazolines.

The phosphorus and sulfur can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes, phosphorodiethionyl disulfide and sulfurized jojoba oil. The phosphites include the dibutyl, dihexyl, dioctyl, didecyl and similar phosphites. Phosphate esters containing 4 to 20 carbon atoms in each hydrocarbyl group, such as tributyl phosphate, tridecyl phosphate, tricresyl phosphate and mixtures of such phosphates, can also be used. Compounds containing both sulfur and phosphorus can also be used such as phosphorodithionyl disulfide. Related components and/or mixtures of each of the above type phosphorus and/or sulfur compounds can be used.

In summary, it is essential to the practice of this invention, in which greases having improved dropping points are obtained, that at least the borated catechol compounds and the hydroxy-containing thickener be included in the grease composition. Thus:

first, with respect to the preparation of the grease, the thickener will have at least about 15 percent by weight of a metal or non-metal hydroxyl-containing soap therein, the total thickener being from about 5 percent to about 20 percent by weight of the grease composition;

second, there will be added to the grease from about 0.1 percent to about 10 percent by weight, preferably about 0.5 percent to about 2.0 percent of a borated catechol compound or mixture of borated catechol compounds, and as a third component optionally, the composition may have therein from 0.2 percent to about 10 percent by weight, preferably from 1 percent to 2 percent by weight, of phosphorus- and sulfur-containing compounds or a mixture of two or more compounds which separately supply the phosphorus and sulfur moieties. If separate compounds are used, an amount of the mixture equivalent to the above concentration levels is used to supply desired amounts of phosphorus and sulfur. These optional third components can be included to provide further substantial improvements in the dropping point.

Base oils used in the grease are mineral, synthetics, other hydrocarbon liquids or mixtures of these. In addition, oxygen-containing fluids can be used such as dibasic acid esters, polyol esters, polyglycols, or phosphate esters. The alkyl benzene-type lubricants are also included. Other fluids that may be used are halogenated fluids, silicones, silicate esters, or polyphenyl ethers. These lubricant fluids can be mixed or used alone as the base oil portion of the grease. In general, mineral oils, both paraffinic, naphthenic and mixtures thereof, may be of any suitable lubricating viscosity range, as for example, from about 45 SSU at 100° F. to about 6000 SSU at 380° C. (100° F.), and preferably from about 50 to about 250 SSU at 210° F. These oils may have viscosity indexes ranging to about 100 or higher. Viscosity indexes from about 70 to about 95 are preferred. The average molecular weights of these oils may range from about 250 to about 800. In making the grease, the lubricating oil from which it is prepared is generally employed in an amount sufficient to balance the total grease composition, after accounting for the desired quantity of the thickening agent, and other additive components to be included in the grease formulation.

In instances where synthetic oils are desired, in preference to mineral oils, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

The metallic soap grease compositions containing one or more of the borated friction reducing compounds and hydroxy-containing soap thickeners and, optionally, one or more of the sulfur and phosphorus combinations described herein provide advantages in increased dropping point, improved grease consistency properties, antirust characteristics and potential antifatigue, antiwear and antioxidant benefits unavailable in any of the prior greases known to us. The grease of this invention is unique in that it can be preferably manufactured by the admixture of additive quantities of the borated catechol compounds to the fully formed soap grease after completion of saponification.

EXAMPLES

To demonstrate the improved dropping point achieved with the combination of a hydroxy bearing thickener and a borated friction reducing agent the following greases were prepared.

EXAMPLE A

Fully Formulated Lithium Hydroxystearate Grease

This example illustrates the preparation of a grease containing a hydroxy-bearing thickener and a phosphorus-sulfur compound, but lacking the borated compound. This grease approximates a prior art or state of the art grease.

A lithium hydroxystearate grease thickener was prepared by a saponifying mixture containing 50 weight percent of 12-hydroxystearic acid in a mixture of the acid and the glycerine thereof with lithium hydroxide in a mineral oil vehicle at about 177° C. (351° F.) in a closed contactor. After the thickener had been depressured and dehydrated in an open kettle, sufficient mineral oil was added to reduce the thickener content to about 9.0%. After the grease had cooled to 99° C. (210° F.), a typical grease additive package, consisting of an amine antioxidant, phenolic antioxidant, metallic dithiophosphate, (phosphorodithioate) sulfur-containing metal deactivator and nitrogen containing antitrust additives, was added. This produced a fully formulated hydroxyl-containing soap grease. The dropping point of this formulated grease was 202° C. (395° F.). The grease was tested for dropping point to compare it with greases formulated according to this invention.

EXAMPLE B

Lithium Hydroxystearate Base Grease

This example illustrates the preparation of a grease containing a hydroxy-bearing thickener but without any additive package of sulfur and phosphorus compounds. This grease approximates a prior art grease without additives.

A lithium hydroxystearate-thickened base grease was prepared as generally described for Example A. No additive package was added to the grease. After reduction of the thickener content to about 10%, the grease (without additives) was cooled and held for subsequent testing. The dropping point of this base grease was 202° C. (395° F.).

EXAMPLE C

Lithium Stearate/Palmitate-Thickened Base Grease

A lithium stearate/palmitate (50% stearate/50% palmitate) base grease not containing any hydroxyl groups in the soap thickeners was prepared for evaluation as generally described in Example B. The total thickener content was about 10%. The dropping point was 207° C. (404° F.).

The effect of blending in two percent of each of the boron compounds described above into the hydroxystearate thickened grease and into the nonhydroxyl-containing stearate/palmitate-thickened grease was tested by measuring the dropping point of the mixed greases. Other blends of the greases were also tested. The test data is summarized in the accompanying table. It will be noted that the combination of hydroxyl bearing thickener and borated compound results in a grease of greatly improved dropping point. The further addition of sulfur and phosphorus compounds acted also to increase the dropping point.

EXAMPLE I

Preparation of Boronated Additives (a) Catechol-Borate Compounds (Mixed Alcohol Borates).

Di-tetradecyl alkylated catechol was prepared by the reaction of 526 grams of catechol with 1875 grams of 1-tetradecene and 500 grams of toluene using 50 grams of acidic catalyst (Super Filtrol) at 170°-180° C. When the reaction was completed, as monitored by vapor phase chromatography, the solvent was removed by distillation and the product was filtered through diatomaceous earth. The product was primarily dialkylated catechol with ~11% monoalkylated catechol and lesser quantities of tetradecene and oligomers of tetradecene. A portion of this product was reserved for the prep described in (b) below.

Approximately 90 grams of this catechol product, 30 grams of toluene, and 22 grams of boric acid were charged to a reactor equipped with heater, agitator and Dean-Stark tube with condenser. The reactants were heated at ~150° C. over a period of ~6 hours until water evolution ceased. A total of 13 grams of water was collected. Approximately 37.5 grams of mixed linear $C_{12}-C_{15}$ alkanols (commercially obtained as Neodol 25 from Shell Chemical Company) were added and the reaction was continued at ~150° C. for 4 more hours. An additional 5 grams of water was evolved. The solvent was removed by distillation and the product was filtered through diatomaceous earth. The product contained approximately 2.5% boron.

(b) (Mixed Alkylated Catechol-Mixed Amine Borate).

Approximately 100 grams of the catechol of the reserved catechol product described above, 75 grams of toluene, and 20 grams of boric acid were reacted at approximately 130° C. for approximately 6 hours (as generally described in Example (a) until water evolution ceased. Approximately 56 grams of oleylamine were added and the reaction was continued for 2 more hours until water evolution again ceased. The solvent was removed by vacuum distillation at approximately 140° C., and the product was filtered through diatomaceous earth. The product contained 1.7% boron.

TABLE

| Grease Composition | Borated Compound | % of Borated Compound in Composition | % of Zinc Dialkyl Thiophosphate | Dropping Point ASTM D 2265 |
|---|---|---|---|---|
| Example A - Hydroxy-bearing thickener & phosphorus-sulfur compound | | 0 | 1.5 | 202° C. (395° F.) |
| Example B - Hydroxy-bearing thickener. No added phosphorus or sulfur or other additives | | 0 | 0 | 202° C. (395° F.) |
| Example C - Lithium stearate/palmitate thickener. No hydroxy-bearing thickener or added sulfur or phosphorus compounds | | 0 | 0 | 207° C. (404° F.) |
| Example B-1 | Catechol-alcohol borate (I-(a) | 2% | 0 | 243° C. (469° F.) |
| Example B-2 | Catechol-alcohol borate (I-(a) | 2% | 1.5% | 302° C. (575° F.) |
| Example C-1 | Catechol- | 2% | 0 | 205° C. |

TABLE-continued

| Grease Composition | Borated Compound | % of Borated Compound in Composition | % of Zinc Dialkyl Thiophosphate | Dropping Point ASTM D 2265 |
|---|---|---|---|---|
| | alcohol borate (I-(a) | | | (401° F.) |
| Example B-3 | Catechol-amine borate (I-(b) | 2% | 0 | 254° C. (489° F.) |
| Example B-4 | Catechol-amine borate (I-(b) | 2% | 1.5% | 309° C. (589° F.) |
| Example C-2 | Catechol-amine borate (I-(b) | 2% | 0 | 199° C. (390° F.) |

What is claimed is:

1. A grease composition comprising a lubricating component, between about 3 and about 20 percent by weight of a hydroxy-containing thickener and between about 0.5 and about 10 percent by weight of a borated catechol compound having the structure:

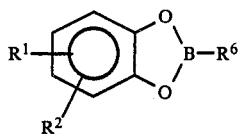

where $R^1$ and $R^2$ are each hydrogen or a $C_1$-$C_{40}$ hydrocarbon radical and $R^6$ is hydrogen or a hydroxyl.

2. The composition of claim 1 wherein said grease contains between about 0.5 and about 10 percent by weight of phosphorus and sulfur containing compounds.

3. The composition of claim 1 wherein said borated catechol compound is the reaction product of an alkylated catechol and boric acid.

4. The composition of claim 1 wherein said hydroxy-containing thickener is lithium hydroxystearate.

5. The composition of claim 1 wherein the lubricating component is mineral oil, synthetic oil, or a mixture thereof.

6. The composition of claim 5 wherein the synthetic oils are polyglycols, synthetic hydrocarbons, alkyl benzenes, dibasic acid esters, polyol esters, phosphate esters or mixtures thereof.

7. The composition of claim 2 wherein said phosphorus and sulfur compound is zinc dialkyldithiophosphate.

8. A method for elevating the dropping point of a grease composition containing between about 3 and about 20 percent by weight of the composition of a hydroxy-containing thickener comprising adding to said composition between about 0.5 and about 10 percent by weight of a borated catechol compound of the structure:

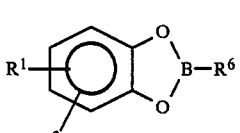

where $R^1$ and $R^2$ are each hydrogen or a $C_1$-$C_{40}$ hydrocarbon radical and $R^6$ is hydrogen or a hydroxyl, the hydroxy-containing thickener and borated catechol compound being present in sufficient quantities to effect an increase in the dropping point of said grease.

9. The method of claim 8 wherein a sulfur-phosphorus containing material is also included in the grease compositions.

10. The method of claim 8 and adding to said grease composition one or more compounds containing sulfur and phosphorus.

11. In a method for making a grease composition wherein a liquid lubricant is mixed with a thickening agent, the improvement comprising including in said grease composition between about 3 and about 20 percent by weight of a hydroxy-containing thickener and between about 0.5 and about 10 percent by weight of a borated catechol compound of the structure:

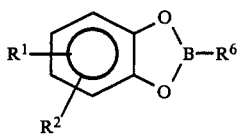

where $R^1$ and $R^2$ are each hydrogen or a $C_1$-$C_{40}$ hydrocarbon radical and $R^6$ is hydrogen or a hydroxyl, the hydroxy-containing thickener and borated catechol compound being present in sufficient quantities to effect an increase in the dropping point of said grease.

12. The method of claim 11 and adding one or more compounds containing sulfur and phosphorus.

13. A grease composition comprising a lubricating component, between about 3 and about 20 percent by weight of a polyhydroxy-containing thickener and between about 0.5 and about 10 percent by weight of a borated catechol compound.

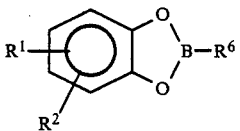

where $R^1$ and $R^2$ are each hydrogen or a $C_1$-$C_{40}$ hydrocarbon radical and $R^6$ is hydrogen or a hydroxyl.

* * * * *